US00PP27172P2

(12) United States Plant Patent
van Zoest

(10) Patent No.: US PP27,172 P2
(45) Date of Patent: Sep. 20, 2016

(54) ***CLEMATIS* PLANT NAMED 'ZO09113'**

(50) Latin Name: ***Clematis* hybdrid**
Varietal Denomination: Zo09113

(71) Applicant: Jan van Zoest, Boskoop (NL)

(72) Inventor: Jan van Zoest, Boskoop (NL)

(73) Assignee: J. van Zoest Beheer B.V., Boskoop (NL)

( * ) Notice: Subject to any disclaimer, the term of this patent is extended or adjusted under 35 U.S.C. 154(b) by 119 days.

(21) Appl. No.: 14/544,323

(22) Filed: Dec. 23, 2014

(51) Int. Cl.
*A01H 5/02* (2006.01)

(52) U.S. Cl.
USPC ..... Plt./228

(58) Field of Classification Search
USPC ..... Plt./228
See application file for complete search history.

*Primary Examiner* — June Hwu
(74) *Attorney, Agent, or Firm* — Penny J. Aguirre

(57) ABSTRACT

A new cultivar of hybrid *Clematis*, 'Zo09113', that is characterized by its almost upright facing flowers, its flowers with bicolored tepals with white centers and purple margins that retain their color with very little or no fading, its sterility, and its cold hardiness to at least U.S.D.A. Zone 5.

2 Drawing Sheets

Botanical classification: *Clematis* hybrid.
Variety denomination: 'Zo09113'.

BACKGROUND OF THE INVENTION

The present invention relates to a new and distinct cultivar of *Clematis* of hybrid origin (*Viticella* Group) and will be referred to hereafter by its cultivar name 'Zo09113'. 'Zo09113' is grown as an herbaceous climber for landscape use and as a flowering potted plant for the terrace.

'Zo09113' is derived from an ongoing breeding program by the Inventor in his nursery in Boskoop, The Netherlands. The goal of the selection was to select a hardy climber with uniquely colored flowers, that is easy to grow and propagate and that could be grown for different purposes. 'Zo09113' was selected in 2009 and arose from a controlled cross made in 2006 between unnamed and unpatented plants from his breeding program; the female parent designated as No. 19990039 and the male parent designated as No. 20050163.

Asexual propagation of the new cultivar was first accomplished by internodial stem cuttings under the direction of the Inventor in Boskoop, The Netherlands in 2010. Asexual propagation by internodial stem cutting has determined that the characteristics of the new cultivar are stable and are reproduced true to type in successive generations.

SUMMARY OF THE INVENTION

The following traits have been repeatedly observed and represent the characteristics of the new cultivar as grown outdoors and observed for four years in Boskoop, The Netherlands. These attributes in combination distinguish *Clematis* 'Zo09113' as a unique cultivar of *Clematis*.

1. 'Zo09113' exhibits almost upright facing flowers.
2. 'Zo09113' exhibits bicolored tepals with white centers and purple margins.
3. 'Zo09113' exhibits flowers that retain their color with very little or no fading.
4. 'Zo09113' is sterile and no seed is produced.
5. 'Zo09113' is cold hardy to at least U.S.D.A. Zone 5.

'Zo09113' differs from its female parent in having flowers that are almost upright and nodding flower buds while the female parent has upright flowers and upright flower buds. 'Zo09113' differs from its male parent in having larger flowers with mostly 6 tepals (sometimes 4-5) and bicolored while the male parent has smaller flowers with 4-5 tepals and are one color.

'Zo09113' can be most closely compared to the cultivars *Clematis* 'Minuet' (not patented) and *Clematis* 'Walenburg' (not patented), differences are described in TABLE 1

TABLE 1

| *Clematis* cultivar | Characteristic Description | | 'Zo09113' |
|---|---|---|---|
| 'Minuet' | Flower size | 4-5 cm | 6-9 cm |
| 'Minuet' | Tepal number | 4 | 6 (4-5 more rarely) |
| 'Minuet' | Flower shape | Campanulate | Almost spreading |
| 'Minuet' | Flower aspect | Nodding | More or less upright |
| 'Walenburg' | Flower size | 5-6 cm | 6-9 cm |
| 'Walenburg' | Tepal number | 4 | 6 (4-5 more rarely) |
| 'Walenburg' | Flower shape | Campanulate | Almost spreading |
| 'Walenburg' | Flower aspect | Nodding | More or less upright |

BRIEF DESCRIPTION OF THE DRAWING

The accompanying colored photographs illustrate the overall appearance and distinct characteristics of the new *Clematis*. The photographs were taken of a three year-old plant of 'Zo09113' as grown in a one-gallon container in Boskoop, The Netherlands.

The photograph in FIG. 1 shows the flowers.

Figure 1:
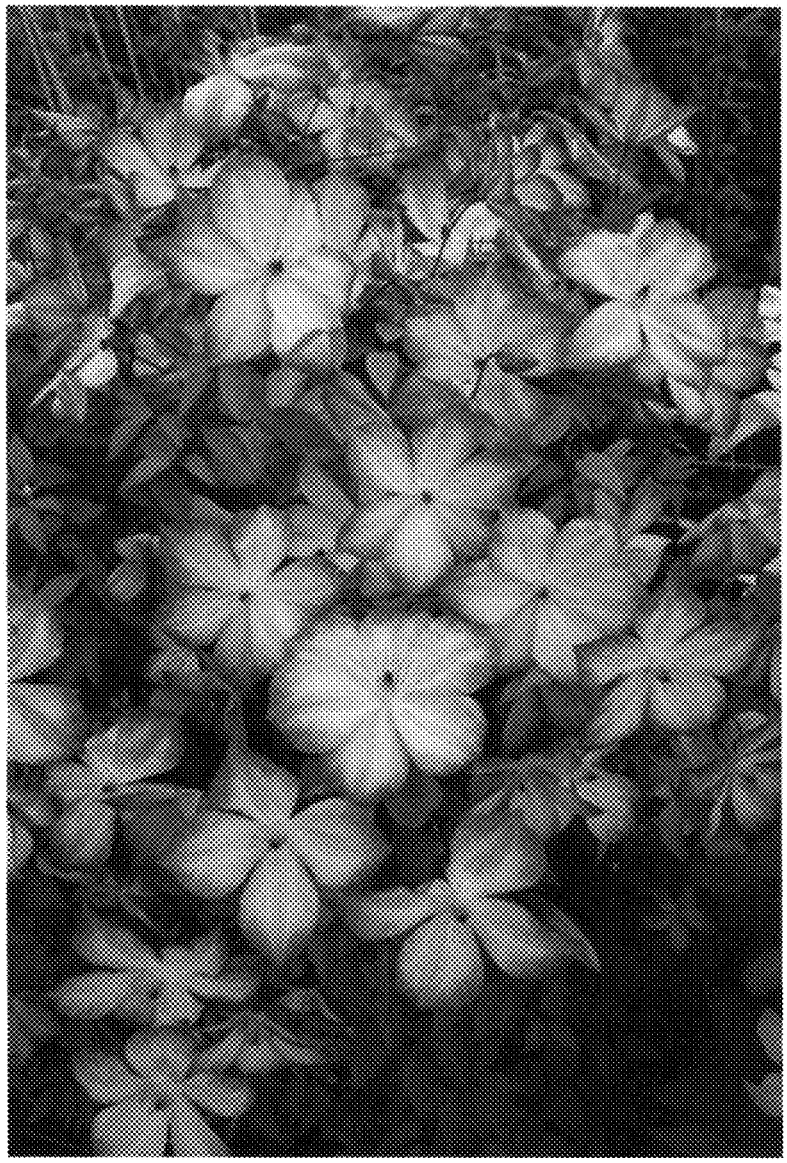
Figure 2:
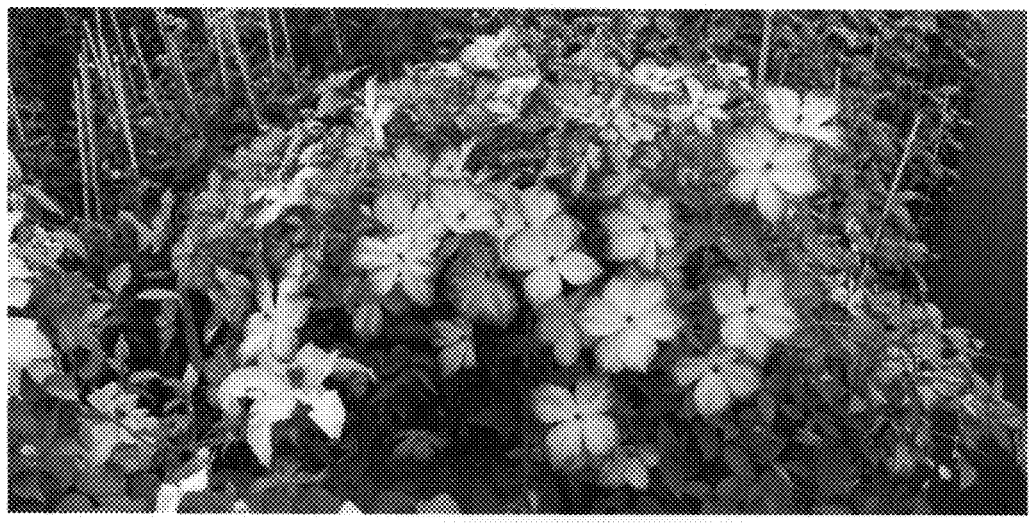

The photograph in FIG. 2 shows the habitus and leaves.

Figure 3:
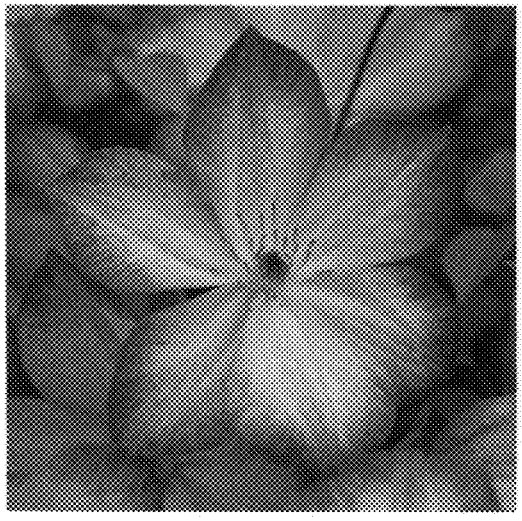

The photograph in FIG. 3 shows the inside of the flower with a close up of the stamens and pistils.

Figure 4:
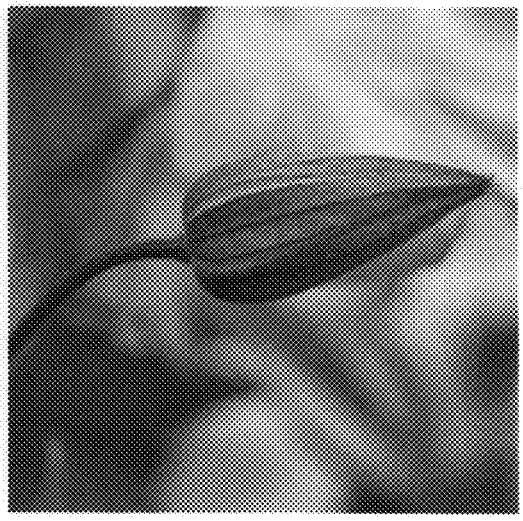

The photograph in FIG. 4 shows the flower bud.

The colors of the photographs are as close as possible with the digital photography techniques available, the color values cited in the detailed botanical description accurately describe the colors of the new *Clematis*.

DETAILED BOTANICAL DESCRIPTION

The following is a detailed description of three year-old plants of 'Zo09113' as grown outdoors in full sun in one-gallon containers at a nursery in Boskoop, The Netherlands. The phenotype of the new cultivar may vary with variations in environmental, climatic and cultural conditions, as the cultivar has not been tested under all possible environmental conditions. The color determination is in accordance with The 2001 R.H.S. Color Chart, London, England, except where general color terms of ordinary dictionary significance are used.

General description:

*Botanical classification.*—*Clematis 'Zo*09113' (classified in the *Viticella* Group).

*Blooming period.*—From late spring to late summer.

*Plant habit.*—Herbaceous climber.

*Height and spread.*—Three year-old plant is about 20 cm in width at the base and 3 m in height when pruned hard in late winter.

*Cold hardiness.*—At least to U.S.D.A. Zone 5.

*Culture.*—Moist but well-drained soils in full sun with the roots shaded.

*Diseases and pests.*—Susceptibility to powdery mildew caused by *Erysiphe polygoni* is unknown, no pest problems have been observed.

*Root description.*—Fleshy.

Growth and propagation:

*Propagation.*—Internodial soft wood cuttings from vegetative shoots.

*Root initiation.*—Roots develop in 5 weeks in summer under greenhouse conditions.

*Time required for root development.*—75 to 90 days to develop a 7-cm container from a 5-cm cutting.

*Growth rate.*—Vigorous and very free flowering in the landscape.

Stem description:

*Shape.*—Round and 6-ribbed.

*Stem color.*—173A.

*Stem size.*—Up to 3 m in length (including peduncle and terminal pedicel), 2 to 4 mm in diameter.

*Stem surface.*—Sparsely covered with hairs.

*Internode length.*—Up to 14 cm in length.

*Branching.*—Branching from the base.

Foliage description:

*Leaf arrangement.*—Opposite.

*Leaf division.*—Ternate or pinnate.

*Leaf size.*—Up to 15 cm in length and 12 cm in width.

*Leaf attachment.*—Petiolate.

*Leaf shape.*—Elliptic.

*Leaf base.*—Base obtuse to subcordate.

*Leaf apex.*—Acuminate.

*Leaf fragrance.*—Clearly a "sharp" fragrance when crushed.

*Leaf venation.*—Upper surface just slightly reticulate, lower surface just reticulate, color similar to leaf color on upper and lower surface.

*Leaf margin.*—Entire.

*Leaf surface.*—Upper surface; glabrous but sometimes a few short hairs on the midvein towards the apex, lower surface; glabrous.

*Leaf color.*—Upper surface; 146A sometimes flushed N79C, lower surface; 146B.

*Petioles.*—1 to 6 cm in length, 1 mm in diameter, 146A stained 79D in color, round but canaliculate above in shape, surface glabrous with a few hairs.

*Petiolules.*—Sessile to 0.3 to 3.5 cm in length, surface glabrous with a few hairs.

Inflorescence description:

*Inflorescence type.*—Solitary or a 3-5 flowered dichasial cyme.

*Inflorescence arrangement.*—Terminal and axillary on young shoots.

*Peduncles.*—4 to 6 cm in length, N79B in color, round, surface slightly 6 ribbed and glabrous with a few short hairs.

*Pedicels.*—6 to 9 cm in length, N79B in color, round in shape, surface slightly ribbed and glabrous with a few short hairs.

*Flower buds.*—Nodding but more or less upright when opening, lanceolate in shape, apex acuminate, base obtuse, 146A in color flushed N82C with ribs 86B, surface sparsely hairy with villous seams.

*Flower fragrance.*—Not fragrant.

*Lastingness of the flowers.*—Individual flowers last up to about 6 to 8 days until the first tepal drops, followed later by the stamens.

*Flower quantity.*—Up to 30 per stem.

*Flower type.*—Almost spreading.

*Flower aspect.*—More or less upright.

*Flower size.*—6 to 9 cm in diameter and 4 cm in depth.

*Flower sex.*—Bisexual.

*Tepal number.*—Usually 6, more rarely 4 or 5.

*Tepal shape.*—Obovate.

*Tepal apex.*—Acute.

*Tepal base.*—Cuneate.

*Tepal margin.*—Entire.

*Tepal surface.*—Inner surface; glabrous, outer surface; glabrous with a few hairs in the middle and villous margin.

*Tepal color.*—Inner surface; 155A and flushed with N82C along the midribs and towards the margin, margin N82B, outer surface; center N82C with 86C ribs, surrounding the center portion N87D becoming darker towards the margin N87A.

*Tepal size.*—Up to 4.5 cm in length and an average of 3.5 cm in width.

Reproductive organs:

*Gynoecium.*—Average of 15 to 25 pistils, up to 1.2 cm in length, ovary 145A in color with glabrous surface, style is N79B in color and only plumose above the ovary (otherwise glabrous), stigma N79C in color and straight.

*Androcoecium.*—Average of 12 stamens, filaments are 0.4 to 0.7 cm in length, 0.1 cm in width and linear in shape, surface is glabrous, color upper portion 13D and 155B at the base; anthers are 0.4 cm in length, 0.5 mm in width, linear in shape, and 62D in color; connective not elongated, apex acute, surface glabrous and 60C in color.

*Seed.*—Seed is not formed, observed to be sterile.

It is claimed:

1. A new and distinct cultivar of *Clematis* plant named 'Zo09113' as herein illustrated and described.

* * * * *